US010512915B2

(12) United States Patent
Sano et al.

(10) Patent No.: US 10,512,915 B2
(45) Date of Patent: Dec. 24, 2019

(54) NUCLEIC ACID AMPLIFIER AND NUCLEIC ACID INSPECTION DEVICE EMPLOYING THE SAME

(75) Inventors: Minoru Sano, Hitachinaka (JP); Yoshiyuki Shoji, Mito (JP); Masato Ishizawa, Hitachinaka (JP); Kimikazu Sugiyama, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 859 days.

(21) Appl. No.: 13/696,444

(22) PCT Filed: Apr. 28, 2011

(86) PCT No.: PCT/JP2011/060406
§ 371 (c)(1),
(2), (4) Date: Dec. 5, 2012

(87) PCT Pub. No.: WO2011/138925
PCT Pub. Date: Nov. 10, 2011

(65) Prior Publication Data
US 2013/0078712 A1    Mar. 28, 2013

(30) Foreign Application Priority Data
May 7, 2010    (JP) .................................. 2010-106953

(51) Int. Cl.
*B01L 7/00*    (2006.01)
(52) U.S. Cl.
CPC ...................................... *B01L 7/52* (2013.01)
(58) Field of Classification Search
CPC .......... B01L 7/52; B01L 7/525; B01L 7/5255; B01L 2300/1822; B01L 3/5082; G01N 35/025; G01N 2035/00366
See application file for complete search history.

(56) References Cited

U.S. PATENT DOCUMENTS 5,674,698 A    10/1997  Zarling et al.
5,693,292 A *  12/1997  Choperena .......... G01N 35/0092
                                                          422/63

(Continued)

FOREIGN PATENT DOCUMENTS

CN       1755371 A    4/2006
CN    101334416 A    12/2008
(Continued)

OTHER PUBLICATIONS

Notification of Transmittal of Translation of the International Preliminary Report on Patentability (PCT/IB/338) and an English translation of the International Preliminary Report on Patentability (PCT/IPEA/409) dated Dec. 13, 2012 (eight (8) pages).

(Continued)

*Primary Examiner* — William H. Beisner
*Assistant Examiner* — Danielle B Henkel
(74) *Attorney, Agent, or Firm* — Crowell & Moring LLP

(57) ABSTRACT

A nucleic acid amplifier comprises a holder 3 which is provided with a plurality of temperature control blocks 10 each designed to hold at least one reaction vessel 105 storing a reaction solution. The temperature of the reaction solution in each reaction vessel 105 is controlled individually by using temperature control devices 14 and 15 arranged in each of the temperature control blocks 10. The temperature that is set in each temperature control block 10 and the timing for temperature changes are controlled independently of the temperatures of other temperature control blocks 10. This configuration makes it possible to provide a nucleic acid amplifier and a nucleic acid inspection device (employing the nucleic acid amplifier) capable of processing multiple types of samples differing in the protocol in parallel (parallel processing) and starting a process for a different sample even when there is a process in execution.

25 Claims, 7 Drawing Sheets

(56) References Cited

U.S. PATENT DOCUMENTS

| | | | |
|---|---|---|---|
| 6,359,284 B1 * | 3/2002 | Hayashi | G01N 21/645 250/458.1 |
| 6,633,785 B1 * | 10/2003 | Kasahara | B01L 7/52 435/286.1 |
| 8,815,153 B2 | 8/2014 | Sato | |
| 2003/0008286 A1 * | 1/2003 | Zou | B01J 19/0093 435/6.12 |
| 2003/0044990 A1 | 3/2003 | Seto | |
| 2005/0009070 A1 * | 1/2005 | Arciniegas | B01L 7/52 435/6.11 |
| 2006/0073584 A1 * | 4/2006 | Sasaki | B01L 3/502715 435/288.5 |
| 2006/0228268 A1 | 10/2006 | Heimberg et al. | |
| 2006/0270026 A1 | 11/2006 | Soh et al. | |
| 2007/0077647 A1 * | 4/2007 | Munenaka | B01L 3/502 435/303.1 |
| 2007/0110634 A1 | 5/2007 | Heimberg et al. | |
| 2007/0140926 A1 | 6/2007 | Heimberg et al. | |
| 2007/0184548 A1 | 8/2007 | Tan et al. | |
| 2008/0274511 A1 | 11/2008 | Tan et al. | |
| 2009/0191097 A1 | 7/2009 | Hanafusa et al. | |
| 2009/0258412 A1 | 10/2009 | Moriwaki et al. | |
| 2010/0099581 A1 | 4/2010 | Arciniegas et al. | |
| 2010/0120099 A1 | 5/2010 | Heimberg et al. | |
| 2010/0120100 A1 | 5/2010 | Heimberg et al. | |

FOREIGN PATENT DOCUMENTS

| | | |
|---|---|---|
| EP | 1 216 098 B1 | 9/2000 |
| JP | 2003-75453 A | 3/2003 |
| JP | 2003-511221 A | 3/2003 |
| JP | 2006-242729 A | 9/2006 |
| JP | 2007-503217 A | 2/2007 |
| JP | 2007-185101 A | 7/2007 |
| JP | 2007-333444 A | 12/2007 |
| JP | 2008-185389 A | 8/2008 |
| JP | 2009-254260 A | 11/2009 |
| WO | WO 01/24930 A1 | 4/2001 |
| WO | WO 2004/105947 A2 | 12/2004 |

OTHER PUBLICATIONS

Chinese Office Action dated May 8, 2014 (eight pages).
Corresponding International Search Report with English Translation dated Jun. 7, 2011 (five (5) pages).
Form PCT/IPEA/409 (five (5) pages), 2011.

* cited by examiner

NUCLEIC ACID AMPLIFIER AND NUCLEIC ACID INSPECTION DEVICE EMPLOYING THE SAME

TECHNICAL FIELD

The present invention relates to a nucleic acid amplifier targeted for samples deriving from a biological body and a nucleic acid inspection device employing the nucleic acid amplifier.

BACKGROUND ART

Nucleic acid amplification technology used for inspecting nucleic acid contained in a sample deriving from a biological body includes a technique employing the polymerase chain reaction (hereinafter referred to as a "PCR method"), for example. In the PCR method, a desired type of base sequences can be selectively amplified by controlling the temperature of a reaction solution (mixture of the sample and a reagent) according to preset conditions.

A temperature control device described in Patent Literature 1 is known as an example of conventional technology related to the nucleic acid amplification employing the aforementioned PCR method. The temperature control device comprises a disk-shaped microchip having a bath region into which a reaction solution as the object of the experiment is injected. After the microchip is set at a desired position by rotating the microchip in a circumferential direction in parallel with a stage, the microchip is pushed toward the stage by using a cover member so as to bring the microchip's bath region into contact with one of heat transfer parts that are arranged in the circumferential direction of the stage and set at different temperatures, by which the temperature of the bath region is controlled.

PRIOR ART LITERATURE

Patent Literature

Patent Literature 1: JP-2008-185389-A

SUMMARY OF THE INVENTION

Problem to be Solved by the Invention

In the nucleic acid amplification technology employing the PCR method, the conditions of amplification such as the reagent used for the amplification process, the temperature and the time (protocol) vary depending on the base sequence as the target of amplification. Therefore, when multiple types of samples differing in the base sequence as the target of amplification are processed in parallel, the temperature and the time specified in the protocol for each type of sample have to be set individually.

In the conventional technology described in the above Patent Literature 1, however, only one protocol can be handled at one time and it is impossible to process multiple types of samples differing in the protocol in parallel (parallel processing). Further, even with samples to be processed with the same protocol, processes differing in the starting time cannot be executed in parallel and a new process for a different sample cannot be started until the current process in execution finishes. Therefore, the conventional technology still has room for improvement in terms of processing efficiency, etc.

The object of the present invention, which has been made in consideration of the above problem, is to provide a nucleic acid amplifier capable of processing multiple types of samples differing in the protocol in parallel (parallel processing) and starting a process for a different sample even when there is a process in execution. Another object of the present invention is to provide a nucleic acid inspection device employing such a nucleic acid amplifier.

Means for Solving the Problem

To achieve the above objects, the present invention provides a nucleic acid amplifier for amplifying nucleic acid in a reaction solution as a mixture of a sample and a reagent, comprising: a plurality of temperature control blocks each designed to hold a reaction vessel storing a reaction solution; a temperature control device which is provided to each of the temperature control blocks and controls the temperature of the reaction solution; and a disk-shaped base member, wherein: the base member is arranged to be rotatable, and the temperature control blocks are arranged along the periphery of the base member to be separate from each other.

Effect of the Invention

According to the present invention, multiple types of samples differing in the protocol can be processed in parallel and a process for a different sample can be started even when there is a process in execution.

MODE FOR CARRYING OUT THE INVENTION

Figure 1:
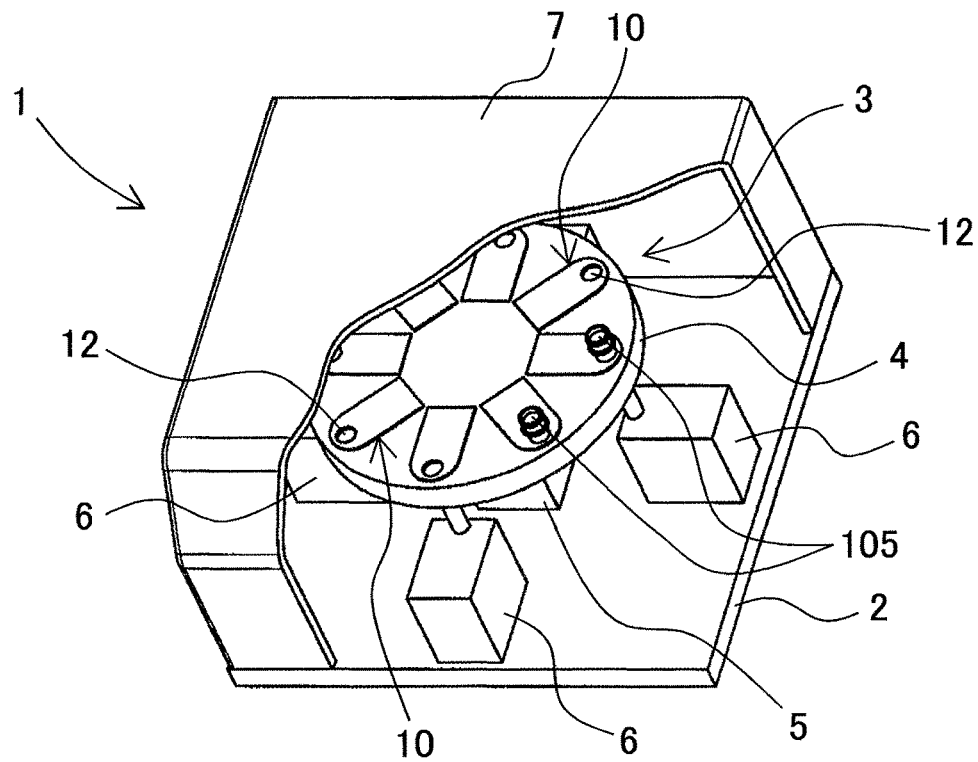
FIG. 1 is a partial sectional perspective view showing the overall configuration of a nucleic acid amplifier in accordance with a first embodiment of the present invention.

Referring now to the drawings, a description will be given in detail of preferred embodiments in accordance with the present invention.

First Embodiment

Figure 14:
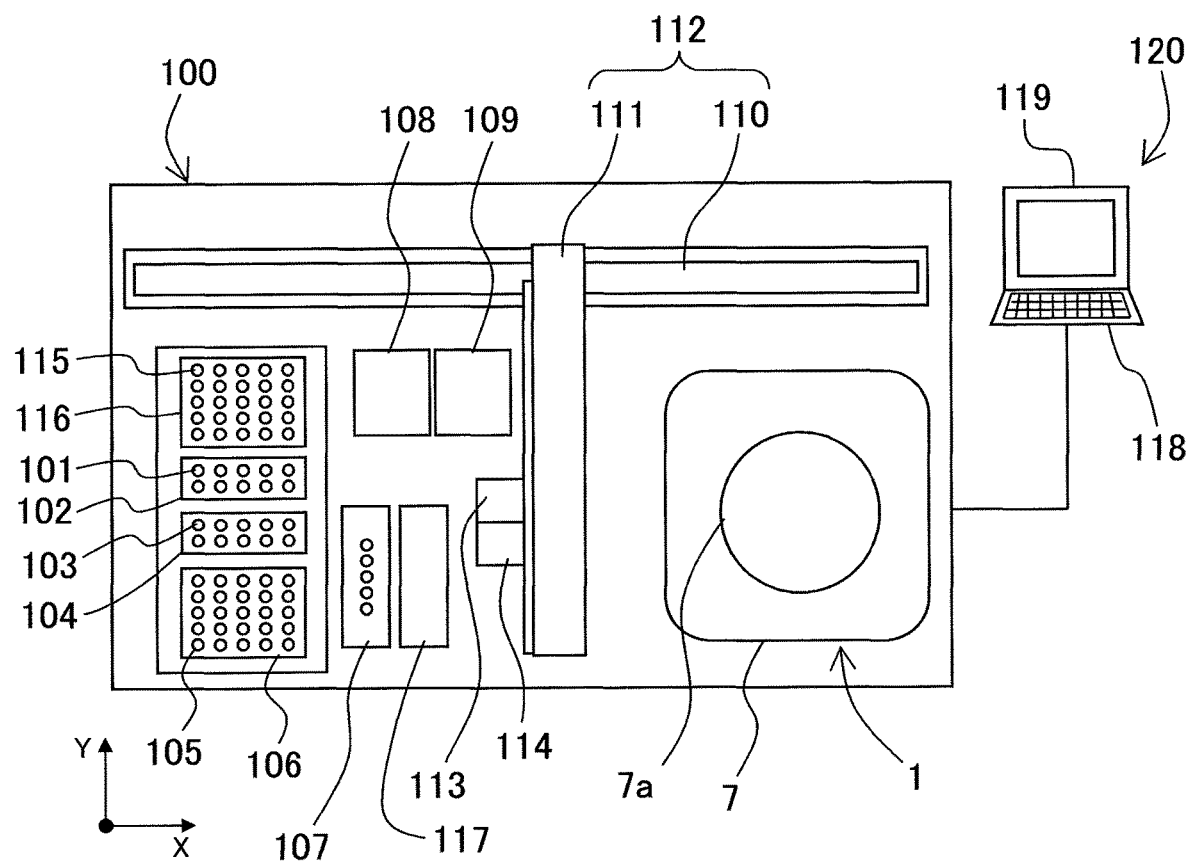
FIG. 14 is a schematic diagram showing the overall configuration of a nucleic acid inspection device which is equipped with a nucleic acid amplifier in accordance with an embodiment of the present invention.

FIG. 14 is a diagram schematically showing the overall configuration of a nucleic acid inspection device 100 in accordance with a first embodiment of the present invention. Referring to FIG. 14, the nucleic acid inspection device 100 comprises a plurality of sample vessels 101 each storing a sample containing nucleic acid as a target of an amplification process, a sample vessel rack 102 storing the sample vessels 101, a plurality of reagent vessels 103 storing various reagents to be added to the samples, a reagent vessel rack 104 storing the reagent vessels 103, a plurality of reaction vessels 105 each of which is used for mixing a sample and a reagent, and a reaction vessel rack 106 storing a plurality of unused reaction vessels 105. The nucleic acid inspection device 100 also comprises a reaction solution adjustment position 107 at which unused reaction vessels 105 are set and the samples and the reagents are dispensed from the sample vessels 101 and the reagent vessels 103 to the reaction vessels 105, a plugging unit 108 for hermetically sealing the reaction vessels 105 (each storing a reaction solution as a liquid mixture of a sample and a reagent) with cover members (not shown), and a stirring unit 109 for stirring the reaction solutions stored in the hermetically sealed reaction vessels 105.

The nucleic acid inspection device 100 further comprises a robot arm device 112, a gripper unit 113, a dispensing unit 114, a plurality of nozzle chips 115, a nozzle chip rack 116, a nucleic acid amplifier 1, a waste box 117, and a control device 120. The robot arm device 112 has a robot arm X-rail 110 provided on the nucleic acid inspection device 100 to extend in an X-axis direction (horizontal direction in FIG. 14) and a robot arm Y-rail 111 arranged to extend in a Y-axis direction (vertical direction in FIG. 14) and attached to the robot arm X-rail 110 to be movable in the X-axis direction. The gripper unit 113, which is attached to the robot arm Y-rail 111 to be movable in the Y-axis direction, grips and conveys a reaction vessel 105 to various parts of the nucleic acid inspection device 100. The dispensing unit 114, which is attached to the robot arm Y-rail 111 to be movable in the Y-axis direction, sucks in a sample stored in a sample vessel 101 or a reagent stored in a reagent vessel 103 and discharges (dispenses) the sample or reagent to a reaction vessel 105 which has been set at the reaction solution adjustment position 107. Each nozzle chip 115 is attached to a part of the dispensing unit 114 that makes contact with a sample or reagent. The nozzle chip rack 116 stores a plurality of unused nozzle chips 115. The nucleic acid amplifier 1 performs a nucleic acid amplification process on the reaction solution stored in each reaction vessel 105. Used nozzle chips 115 and used reaction vessels 105 (after inspection) are discarded to the waste box 117. The control device 120 includes an input device 118 (keyboard, mouse, etc.) and a display device 119 (liquid crystal monitor, etc.) and controls the operation of the entire nucleic acid inspection device 100 including the nucleic acid amplifier 1.

Each sample vessel 101 is managed in terms of the stored sample by using identification information (e.g., bar code) and using positional information (e.g., coordinates) assigned to each position in the sample vessel rack 102. Similarly, each reagent vessel 103 is managed in terms of the stored reagent by using identification information (e.g., bar code) and using positional information (e.g., coordinates) assigned to each position in the reagent vessel rack 104. The identification information and positional information are previously registered and managed in the control device 120. Each reaction vessel 105 is also managed similarly by using identification information and positional information.

Next, the details of the nucleic acid amplifier 1 will be explained below referring to FIGS. 1-4.

Figure 2:
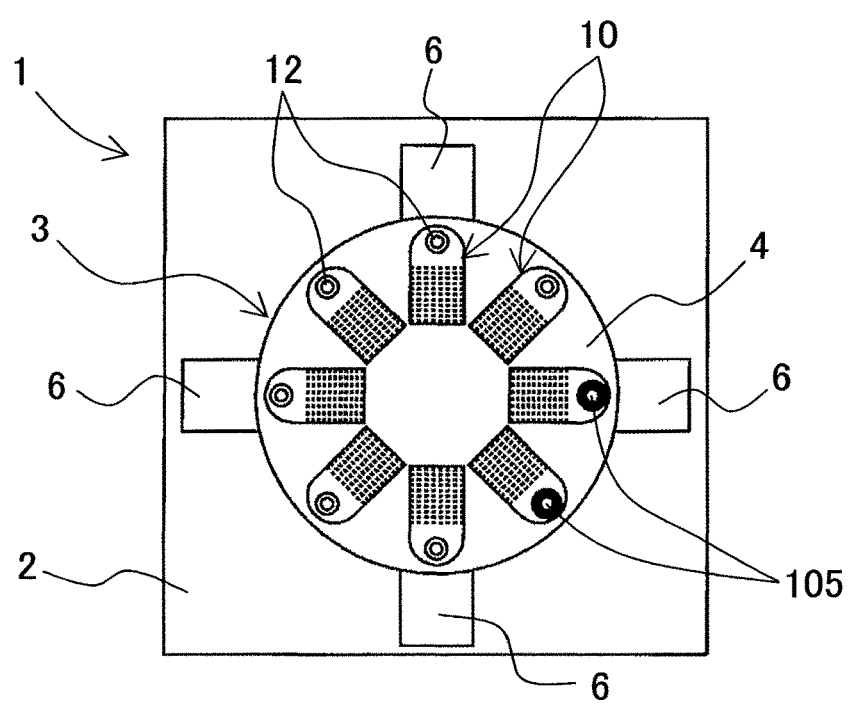
FIG. 2 is a plan view showing the overall configuration of the nucleic acid amplifier in accordance with the first embodiment of the present invention.
Figure 3:
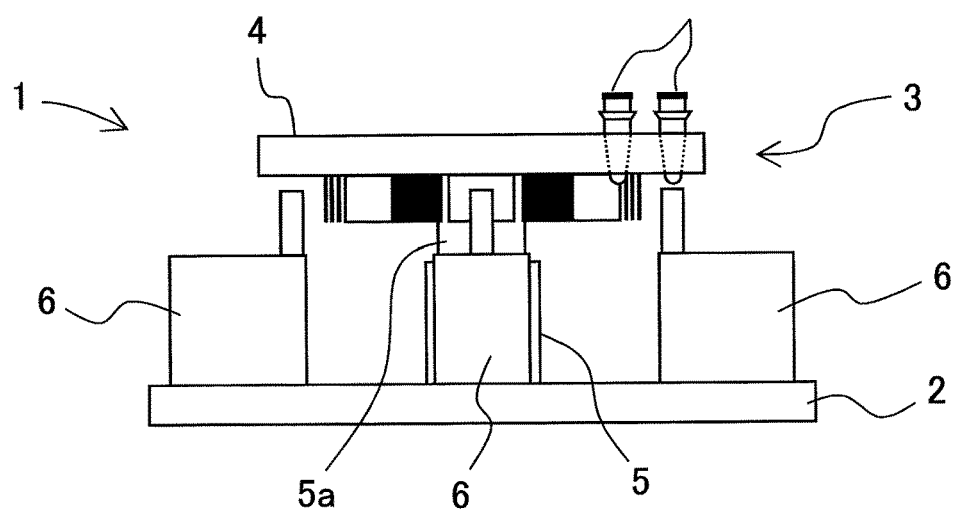
FIG. 3 is a side view showing the overall configuration of the nucleic acid amplifier in accordance with the first embodiment of the present invention.
Figure 4:
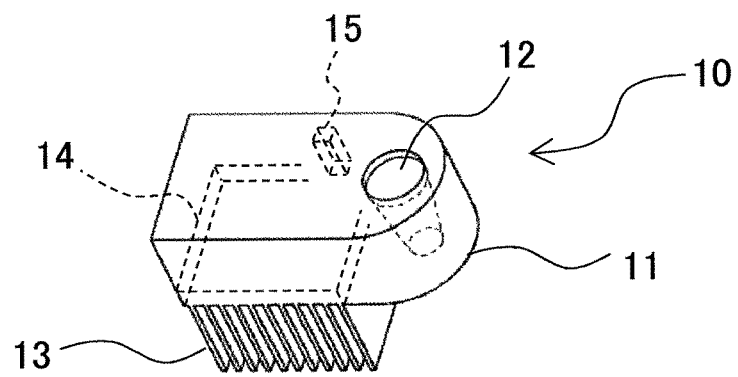
FIG. 4 is a perspective view excerpting a temperature control block in accordance with the first embodiment of the present invention.

FIGS. 1-3 are a partial sectional perspective view, a plan view and a side view showing the overall configuration of the nucleic acid amplifier 1 in accordance with the first embodiment of the present invention. FIG. 4 is a perspective view excerpting and magnifying a temperature control block 10 of a holder 3. In FIGS. 2 and 3, a cover 7 is not shown for convenience of explanation.

Referring to FIGS. 1-3, the nucleic acid amplifier 1 mainly comprises a base 2 serving as the base of the nucleic acid amplifier 1, a holder 3 provided with a plurality of temperature control blocks 10 each having a configuration for holding a reaction vessel 105, fluorescence detectors 6 for detecting fluorescence from the reaction solutions stored in the reaction vessels 105, and a cover 7 covering the holder 3 and the fluorescence detectors 6.

The holder 3 includes a disk-shaped holder base 4 arranged with its central axis pointing upward (upward in FIG. 3) and a plurality of temperature control blocks 10 arranged around the central axis of the holder base 4 and along and inside the periphery of the holder base 4. The holder base 4, which is arranged to be rotatable in the circumferential direction around a rotating shaft 5a at the center, is driven and rotated by a stepping motor 5 serving as a rotary driving device.

The holder base 4 is formed with members excelling in heat insulating properties (e.g. plastic) and configured to reduce interference among the temperatures of the temperature control blocks 10. It is also possible to further reduce the temperature interference by providing a heat insulating layer made of a heat insulating material (e.g., polyurethane foam) between the holder base 4 and the temperature control blocks 10.

As shown in FIG. 4, the temperature control block 10 includes a base 11 serving as the base of the temperature control block 10, a setting position 12 formed like a through hole penetrating the base 11 in the vertical direction (vertical direction in FIG. 3), a Peltier element 14 and a radiation fin 13 provided under the base 11 to serve as a temperature control device, and a temperature sensor 15 arranged in the base 11 for detecting the temperature of the reaction solution in the reaction vessel 105 by measuring the temperature in the vicinity of the setting position 12. A thermistor, a thermocouple, a temperature detecting resistor, etc. can be used for the temperature sensor 15.

The base 11 is formed of a thermal conductor such as copper, aluminum and various types of alloys. The temperature of the reaction vessel 105 held in the setting position 12 of the base 11 is controlled and adjusted by heating and cooling the base 11 by using the Peltier element 14. The radiation fin 13 is provided on a surface of the Peltier element 14 opposite to the base 11 and enhances the heat radiation efficiency of the Peltier element 14. The reaction vessel 105 is inserted into the setting position 12 of the base 11 from above, by which the reaction vessel 105 is held in the temperature control block 10 with its bottom exposed to the outside of the temperature control block 10.

Returning to FIGS. 1-3, one or more fluorescence detectors 6 (four in this embodiment, for example) are arranged along the periphery of the holder 3 at even intervals. Each fluorescence detector 6 is placed below the reaction vessels 105 (below the path of the movement of the reaction vessels 105) and detects fluorescence when a reaction vessel 105 passes over the fluorescence detector 6 due to the rotation of the holder 3. When there are two or more fluorescence detectors 6, the fluorescence detectors 6 perform the detection or measurement of the reaction solutions in the reaction vessels 105 independently from each other.

The fluorescence detector 6 includes an excitation light source (not shown) for applying excitation light to the bottom (exposed part) of the reaction vessel 105 held in the setting position 12 of the temperature control block 10 and a detector element (not shown) for detecting the fluorescence from the reaction solution. In the reaction solution stored in the reaction vessel 105, base sequences as the target of amplification by use of the reagent have been fluorescently labeled. The amount of the base sequences as the target of amplification in the reaction solution is measured with the passage of time by detecting the fluorescence from the reaction solution (caused by the irradiation of the reaction vessel 105 with the excitation light emitted from the excitation light source) with the fluorescence detector 6. The results of the detection are sent to the control device 120. A light-emitting diode (LED), a semiconductor laser (laser diode), a xenon lamp, a halogen lamp, etc. can be used as the excitation light source. A photodiode, a photomultiplier, a CCD, etc. can be used as the detector element.

The cover 7 is employed for the purpose of reducing the incidence of external light onto the fluorescence detectors 6 of the nucleic acid amplifier 1 (light shielding effect) by covering the holder 3 and the fluorescence detectors 6 in cooperation with the base 2. The cover 7 has a gate 7a which can be opened and closed (see FIG. 14). The reaction vessels 105 are loaded/unloaded into/from the inside of the cover 7 (i.e., loaded/unloaded into/from the nucleic acid amplifier 1) via the gate 7a. Incidentally, the gate 7a of the cover 7 is not shown in FIG. 1 for brevity.

The control device 120 controls the operation of the entire nucleic acid inspection device 100. The control device 120 executes the nucleic acid amplification processes based on protocols (set through the input device 118) and using a variety of software, etc. previously stored in a storage unit (not shown), stores analysis results (fluorescence detection results, etc.), operational status of the nucleic acid amplifier 1, etc. in the storage unit, displays the analysis results, the operational status, etc. on the display device 119, and so forth.

The operation in this embodiment configured as above will be described below.

First, as the preparation for the nucleic acid amplification processes, sample vessels 101 each storing a sample containing nucleic acid as the target of the amplification process are stored in the sample vessel rack 102 of the nucleic acid inspection device 100, and reagent vessels 103 storing various reagents (previously determined by the protocols) to be added to the samples are stored in the reagent vessel rack 104. Further, unused reaction vessels 105 are stored in the reaction vessel rack 106, and unused nozzle chips 115 are stored in the nozzle chip rack 116. In this state, the nucleic acid amplification processes are started by operating the control device 120.

In response to the instruction for starting the nucleic acid amplification processes, a necessary number of unused reaction vessels 105 are conveyed by the gripper unit 113 to the reaction solution adjustment position 107. Subsequently, an unused nozzle chip 115 is attached to the dispensing unit 114, and each sample is dispensed from a prescribed sample vessel 101 to reaction vessels 105. Thereafter, the nozzle chip 115 which has been used is discarded to the waste box 117 in order to prevent contamination. Subsequently, also for each reagent, the dispensing to prescribed reaction vessels 105 is carried out in a similar manner, by which each reaction solution is generated through the mixture of a reagent with a sample.

When a necessary number of dispensing operations are finished, the reaction vessels 105 storing the reaction solutions are conveyed by the gripper unit 113 to the plugging unit 108 and hermetically sealed with the cover members. The hermetically sealed reaction vessels 105 are further conveyed to the stirring unit 109 and undergo a stirring process. Each reaction vessel 105 after undergoing the stirring process is conveyed by the gripper unit 113 through the gate 7a of the cover 7 of the nucleic acid amplifier 1, inserted into one of the setting positions 12 of the holder 3 at a prescribed position, and held in the setting position 12. In this step, the holder 3 is driven, rotated and controlled so that a prescribed one of the setting positions 12 is placed at the position of the gate 7a. When there are two or more reaction vessels 105 to be processed, the hermetic sealing with the cover member and the stirring process are conducted to each of the reaction vessels 105, and the hermetically sealed and stirred reaction vessels 105 are successively conveyed to prescribed setting positions 12.

Then, the nucleic acid amplification process is executed by controlling the temperature of a reaction vessel 105 held in the holder 3 in a periodical and stepwise manner by controlling the Peltier element 14 of the temperature control device based on the protocol corresponding to the sample stored in the reaction vessel 105. As above, the PCR method as a type of the nucleic acid amplification technology selectively amplifies a desired type of base sequences by changing the temperature of the reaction solution (mixture of a sample and a reagent) in a periodical and stepwise manner based on the protocol corresponding to each sample. Also when two or more reaction vessels 105 are processed in parallel, each nucleic acid amplification process is started successively when each reaction vessel 105 is held in a setting position 12, and the temperature of each reaction vessel 105 is changed in a periodical and stepwise manner based on the protocol corresponding to each sample. During the nucleic acid amplification process, the amount of the base sequences as the target of amplification in the reaction solution is measured with the passage of time by driving and rotating the holder 3 and detecting the fluorescence from the reaction solution with the fluorescence detector 6. The results of the detection are successively sent to the control device 120.

After a prescribed nucleic acid amplification process is finished, the reaction vessel 105 is conveyed by the gripper unit 113 to the waste box 117 through the gate 7a and discarded to the waste box 117.

Effects achieved in this embodiment configured as above will be described below.

In the nucleic acid amplification technology employing the PCR method, the conditions of amplification such as the reagent used for the amplification process, the temperature and the time (protocol) vary depending on the base sequence as the target of amplification. Therefore, when multiple types of samples differing in the base sequence as the target of amplification are processed in parallel, the temperature and the time specified in the protocol for each type of sample have to be set individually. In the conventional technology, however, only one protocol can be handled at one time and it is impossible to process multiple types of samples differing in the protocol in parallel (parallel processing). Further, even with samples to be processed with the same protocol, processes differing in the starting time cannot be executed in parallel and a new process for a different sample cannot be started until the current process in execution finishes.

In contrast, the nucleic acid amplifier 1 in this embodiment is configured to comprise the holder 3, which is provided with a plurality of temperature control blocks 10 each designed to hold a reaction vessel 105 storing a reaction solution, and to adjust the temperature of each reaction solution with the temperature control device mounted on each temperature control block 10. Therefore, multiple types of samples differing in the protocol can be processed in parallel (parallel processing) and a new process for a different sample can be started even when there is a process in execution. As a result, the processing efficiency can be increased significantly.

Each temperature control block 10 is detachable from the holder base 4, and thus inspection/replacement of temperature control blocks 10 can be conducted with ease when a temperature control block 10 has failed. By changing the shape of the setting position 12 formed in the base of each temperature control block 10, reaction vessels having different shapes can be set on the holder base 4 at the same time. The base 11, the temperature control device 14 and the temperature sensor 15 of any temperature control block 10 can be optimized to deal with a particular analysis item, and the optimized temperature control block 10 can be mounted on the holder base 4. With this configuration, various analysis items can be carried out using the same holder base 4, in a device status optimized for the specified temperatures. Incidentally, a fan may be installed to promote the heat exchange by the radiation fin 13 (forced air cooling). The heat radiation efficiency may be increased further by using a duct for guiding the wind from the fan to a desired position.

In order to suppress the rise in the atmospheric temperature inside the nucleic acid amplifier 1 covered by the cover 7, it is possible to install an intake fan for supplying the outside air to the inside of the cover 7 and an exhaust fan for discharging the air. With this configuration, the atmospheric temperature inside the nucleic acid amplifier 1 can be kept constant and the temperature change (temperature control) of the holder base 4 and the temperature control blocks 10 can be conducted continuously.

Further, to promote the radiation of heat such as the Joule heat caused by the energization of the Peltier elements and the sensors, it is possible to form the holder base 4 and the rotating shaft 5a with materials excelling in heat conductivity (e.g., aluminum), while also increasing the surface areas of the holder base 4 and the rotating shaft 5a, using heat conductive grease for contact interfaces between the members, or increasing the adhesion between the members by reducing the surface roughness at the contact interfaces between the members.

It is also possible to actively promote the heat transmission from the holder base 4 and the rotating shaft 5a to other members by installing heat pipes in/on the holder base 4, the rotating shaft 5a, etc. The heat radiation efficiency can be increased further by properly installing a fin, a fan, a duct, a water-cooling mechanism, etc.

The relative speed between the reaction vessels 105 and the fluorescence detectors 6 during the fluorescence measurement can be controlled by controlling the revolution speed (relative revolution speed) of the holder base 4 with respect to the fluorescence detectors 6. The fluorescence detection may be conducted either by keeping the relative speed at a constant speed or by temporarily stopping a reaction vessel 105 at a position facing a fluorescence detector 6.

Modification

A modification of the first embodiment of the present invention will be described below with reference to FIG. 5.

Figure 5:
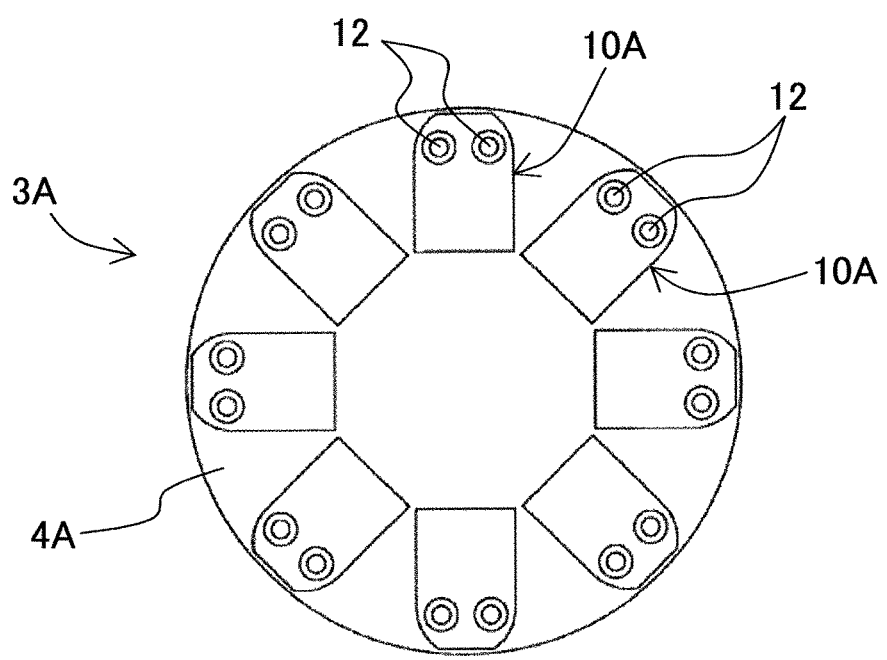
FIG. 5 is a plan view showing a holder in accordance with a modification of the first embodiment of the present invention.

FIG. 5 is a plan view showing a holder 3A in accordance with this embodiment (modification). In FIG. 5, components identical with those explained in the first embodiment are assigned the same reference characters as in the first embodiment and repeated explanation thereof is omitted for brevity. In this embodiment, each temperature control block 10 of the holder 3 in the first embodiment is provided with two or more setting positions 12.

Referring to FIG. 5, the holder 3A in this embodiment includes a disk-shaped holder base 4A arranged with its planar part facing upward and a plurality of temperature control blocks 10A arranged along the periphery of the holder base 4A. Each temperature control block 10A is provided with two or more setting positions 12 (two in this embodiment).

The other configuration is equivalent to that in the first embodiment.

Also in this embodiment configured as above, effects similar to those of the first embodiment can be achieved.

Further, since each temperature control block 10A is configured to be able to hold two or more reaction vessels 105, the nucleic acid amplification processes of two or more reaction solutions according to the same protocol can be conducted at the same time, by which the processing efficiency can be increased further.

Furthermore, since the temperature control range in each temperature control block 10A becomes wider compared to the case with only one setting position 12, it is possible to install a fan integrally in each temperature control block 10A and control the operating status of the fan at times of temperature rise and temperature drop for each temperature control range. Consequently, the speeds of the temperature rise and the temperature drop can be increased.

Second Embodiment

A second embodiment in accordance with the present invention will be described below with reference to FIGS. 6 and 7.

Figure 6:
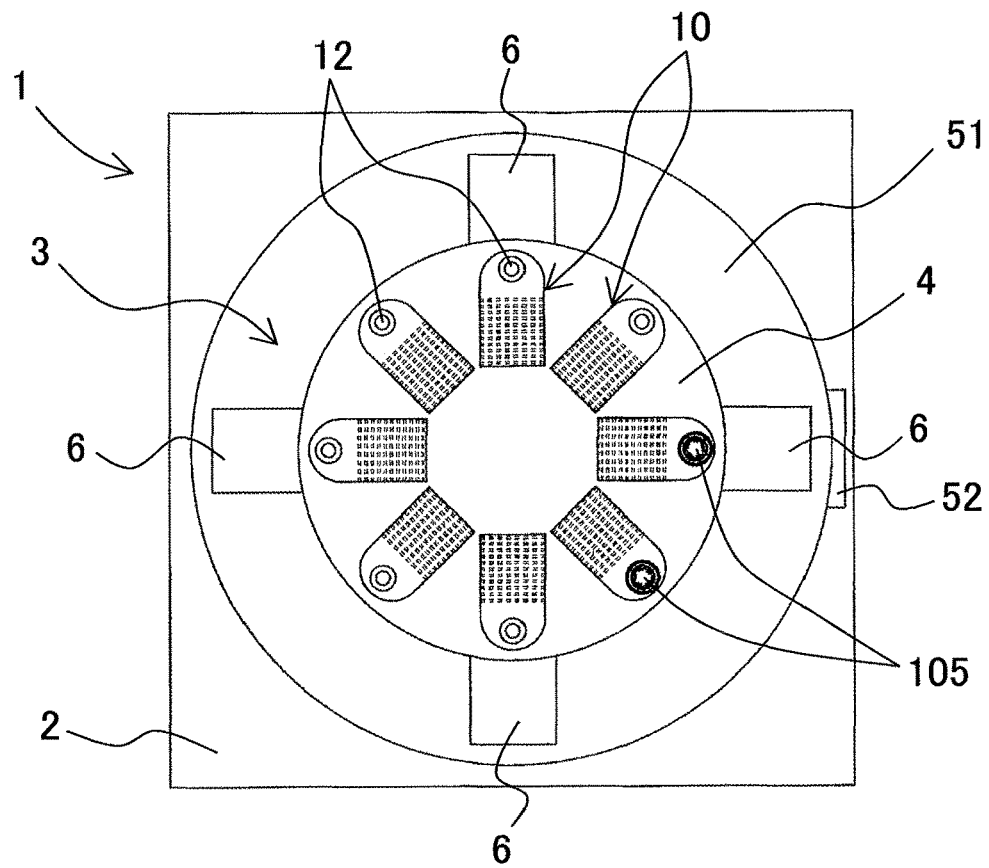
FIG. 6 is a plan view showing a nucleic acid amplifier in accordance a second embodiment of the present invention.
Figure 7:
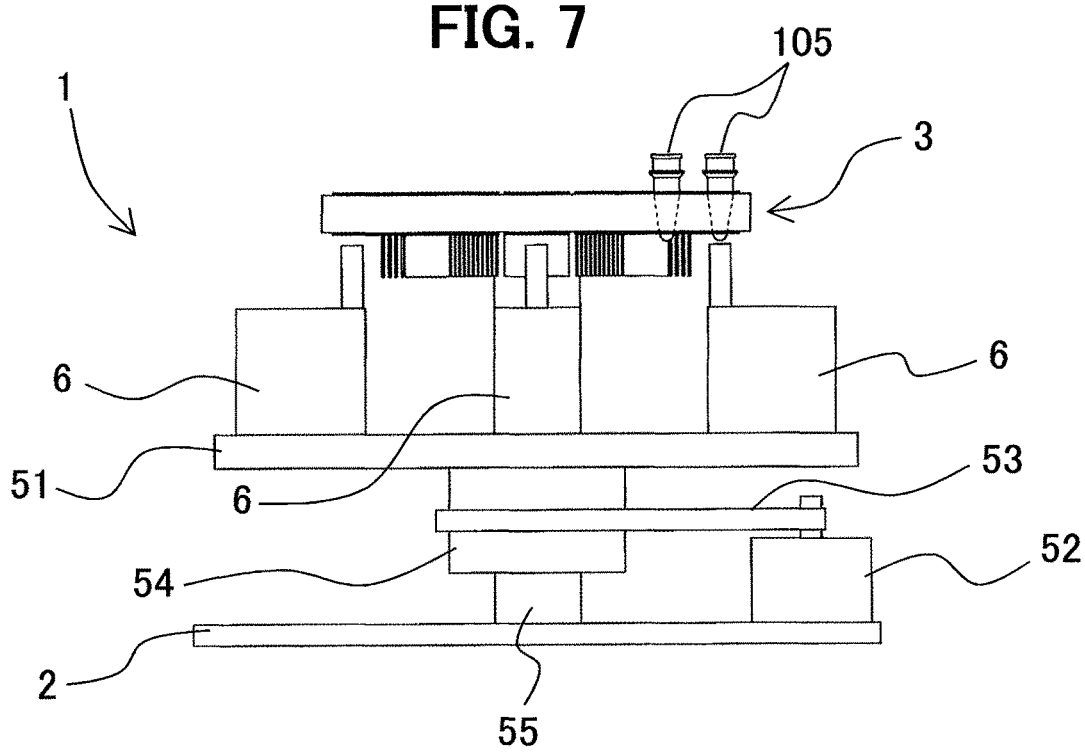
FIG. 7 is a side view showing the nucleic acid amplifier in accordance the second embodiment of the present invention.

FIGS. 6 and 7 are a plan view and a side view showing a nucleic acid amplifier 1 in accordance with this embodiment. In FIGS. 6 and 7, components identical with those explained in the first embodiment are assigned the same reference characters as in the first embodiment and repeated explanation thereof is omitted for brevity. This embodiment is configured to carry out the fluorescence detection for the reaction solutions stored in the reaction vessels 105 by fixing the holder 3 employed in the first embodiment while driving the fluorescence detectors 6 in the circumferential direction of the holder 3. Incidentally, the cover is not shown in FIGS. 6 and 7 for convenience of explanation.

Referring to FIGS. 6 and 7, the nucleic acid amplifier 1 mainly comprises a base 2 serving as the base of the nucleic acid amplifier 1, a holder 3 provided with a plurality of temperature control blocks 10 each having a configuration for holding a reaction vessel 105, fluorescence detectors 6 for detecting the fluorescence from the reaction solutions stored in the reaction vessels 105, and a cover (not shown) covering the holder 3 and the fluorescence detectors 6.

The holder 3 includes a holder base 4 and a plurality of temperature control blocks 10. The holder base 4 is fixed to a base 2 by using a support member 55 provided at the center of the holder base 4.

One or more fluorescence detectors 6 (four in this embodiment, for example) are fixed on a detector base 51 so that the fluorescence detectors 6 are arranged below the reaction vessels 105 and along the periphery of the holder 3 at even intervals. The detector base 51 is coupled to the support member 55 via a detector base rotating shaft 54 arranged coaxially with the support member 55. The detector base 51 is arranged to be drivable and rotatable in the circumferential direction by use of a configuration such as a roller bearing between the support member 55 and the detector base rotating shaft 54. The detector base rotating shaft 54 is linked with a motor 52 (for driving and rotating the detector base rotating shaft 54) via a belt 53. The fluorescence detection is carried out when a fluorescence detector 6 passes under a reaction vessel 105 due to the rotation of the detector base rotating shaft 54 and the detector base 51 driven by the motor 52. When there are two or more fluorescence detectors 6, the fluorescence detectors 6 perform the detection or measurement of the reaction solutions in the reaction vessels 105 independently from each other. The relative speed between the reaction vessels 105 and the fluorescence detectors 6 during the fluorescence measurement can be controlled by controlling the revolution speed (relative revolution speed) of the holder base 4 with respect to the fluorescence detectors 6. The fluorescence detection may be conducted either by keeping the relative speed at a constant speed or by temporarily stopping a fluorescence detector 6 at a position facing a reaction vessel 105.

A cover 7 is used for the purpose of reducing the incidence of external light onto the fluorescence detectors 6 of the nucleic acid amplifier 1 (light shielding effect) by covering the holder 3 and the fluorescence detectors 6 in cooperation with the base 2. The cover 7 has a gate 7a which can be opened and closed (see FIG. 14). The reaction vessels 105 are loaded/unloaded into/from the inside of the cover 7 (i.e., loaded/unloaded into/from the nucleic acid amplifier 1) via the gate 7a. The gate 7a in this embodiment is configured so that the reaction vessels can be set in the setting positions 12 from the outside of the cover 7. The gate 7a may be placed at a position corresponding to a desired setting position 12 (as the target of setting a reaction vessel 105) by expanding the gate 7a or by moving part or all of the cover 7, for example.

Incidentally, while the nucleic acid amplifier 1 in this embodiment is configured to conduct the fluorescence detection of the reaction solutions stored in the reaction vessels 105 by fixing the holder 3 and moving the fluorescence detectors 6 in the circumferential direction of the holder 3, the fluorescence detection of the reaction solutions may also be implemented by configuring both the holder 3 and the fluorescence detectors 6 to be rotatable and controlling the relative rotation of the holder 3 and the fluorescence detectors 6.

The other configuration is equivalent to that in the first embodiment.

Also in this embodiment configured as above, effects similar to those of the first embodiment can be achieved.

Third Embodiment

A third embodiment in accordance with the present invention will be described below with reference to FIGS. 8 and 9.

Figure 8:
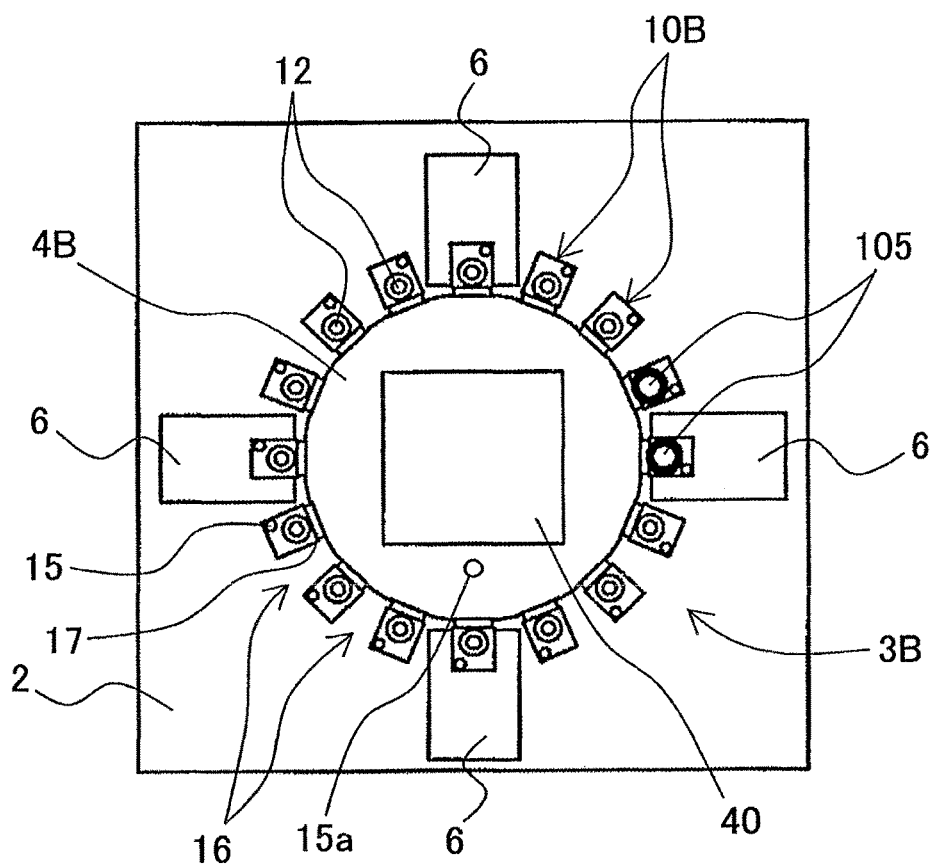
FIG. 8 is a side view showing a nucleic acid amplifier in accordance a third embodiment of the present invention.
Figure 9:
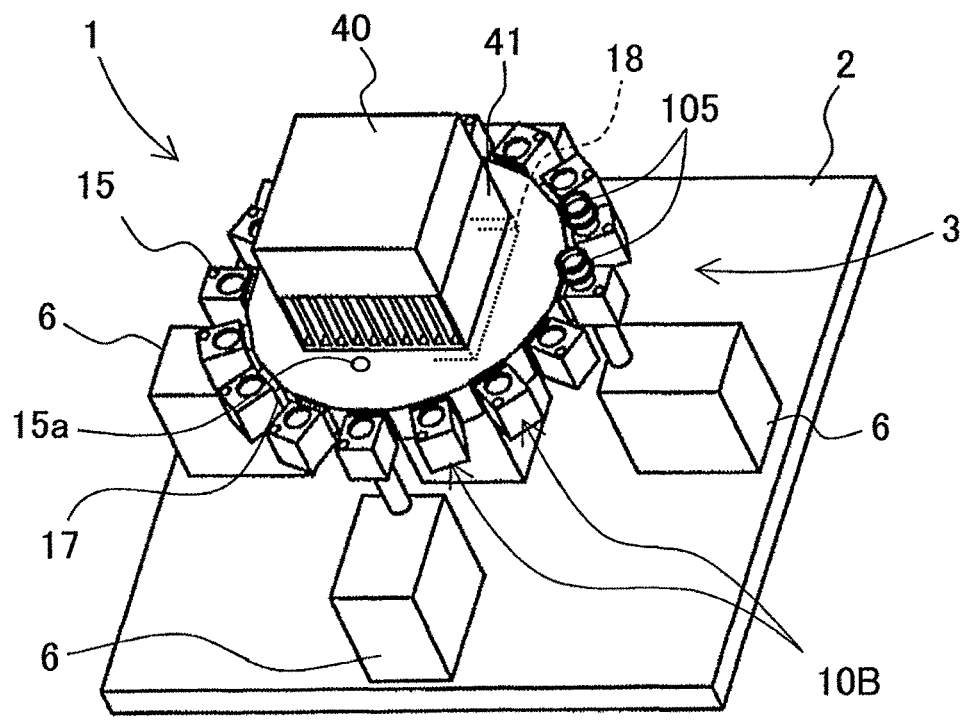
FIG. 9 is a perspective view showing the nucleic acid amplifier in accordance the third embodiment of the present invention.

FIGS. 8 and 9 are a plan view and a perspective view showing a nucleic acid amplifier 1 in accordance with this embodiment. In FIGS. 8 and 9, components identical with those explained in the first embodiment are assigned the same reference characters as in the first embodiment and repeated explanation thereof is omitted for brevity. In this embodiment, the temperature control blocks 10 of the holder 3 employed in the first embodiment are arranged on the periphery of the holder base 4 and notch parts 16 are formed between the temperature control blocks 10 as spaces for heat insulation.

Referring to FIGS. 8 and 9, a holder 3B in this embodiment includes a disk-shaped holder base 4B arranged with its planar part facing upward and a plurality of temperature control blocks 10B arranged in the circumferential direction on the outer surface of the periphery of the holder base 4B. The holder base 4B and the temperature control blocks 10B are formed of a thermal conductor such as aluminum, copper and various types of alloys. The temperature control blocks 10B are formed integrally with the holder 3B. Between adjacent temperature control blocks 10B arranged in the circumferential direction of the holder base 4B, a notch part 16 extending from the periphery toward the center of the holder base 4B is formed. By such spaces provided between the temperature control blocks 10B arranged in the circumferential direction of the holder base 4B, heat isolation properties between the temperature control blocks 10B are enhanced. Each temperature control block 10B is equipped with a Peltier element 17 as a temperature control device and a temperature sensor 15 for detecting the temperature of the reaction solution in the reaction vessel 105 by measuring the temperature in the vicinity of the setting position 12. The Peltier element 17 is installed so that one of its two heat exchanging surfaces closely adheres to the temperature control block 10B and the other heat exchanging surface closely adheres to the holder base 4B. Incidentally, the temperature of the holder base 4B is lower than the temperature control blocks 10B performing the temperature control of the reaction vessels since the temperatures used for the nucleic acid amplification are generally higher than room temperature. This promotes the transmission of heat from each temperature control block 10B to the holder base 4B when the temperature of the temperature control block 10B is lowered, by which the temperature drop can be achieved more quickly. Further, it is possible in this embodiment to set the volume of the holder base 4B larger than that of the temperature control blocks 10B. Since the heat capacity of the holder base 4B can be set sufficiently high just by forming both the holder base 4B and the temperature control blocks 10B with the same material (e.g., aluminum), high heat radiation efficiency of each temperature control block 10B can be achieved. Furthermore, when the holder base 4B performs the heat exchange with two or more temperature control blocks 10B at the same time, the effect of the heat exchange between the holder base 4B and a temperature control block 10B on the heat exchange between the holder base 4B and another temperature control block 10B can be minimized.

Arranged at the center of the holder base 4B are a Peltier element 18 as a temperature control device, a temperature sensor 15a for detecting the temperature in the vicinity of the Peltier element 18, a radiation fin 41 connected with the Peltier element 18, and a fan 40 for sending air to the radiation fin 41. Therefore, heat radiation/absorption efficiency of the Peltier element 17 of each temperature control block 10B can be increased further by keeping the temperature of the holder base 4B at a constant level (e.g., 40° C.) with the temperature control device 18. When the PCR method as a type of the nucleic acid amplification technology is conducted, a prescribed temperature cycle including a temperature rise and a temperature drop is repeatedly applied to the reaction vessel by the temperature control block 10B. By properly setting the temperature of the holder base 4B in this temperature control, the speed of the temperature change can be increased and the balance between the temperature rise speed and the temperature drop speed can be controlled. For example, the temperature drop speed can be increased by controlling the holder base 4B at temperatures lower than the temperature range implemented by the temperature control block 10B. The maximum temperature and the temperature rise speed can be increased by controlling the temperature of the holder base 4B within (between the upper limit and the lower limit of) the temperature range implemented by the temperature control block 10B. Meanwhile, in the NASBA method as a type of the nucleic acid amplification technology, the reaction vessel is kept at a constant temperature (41° C.) with the temperature control block 10. This temperature control can be performed precisely by properly setting the temperature of the holder base 4B. Further, by providing the base 2 and the cover 7 with fans, an air flow is forcefully caused inside the nucleic acid amplifier 1 and the heat insulation effect can be enhanced by the passage of the air flow through the notch parts 16.

The other configuration is equivalent to that in the first embodiment.

Also in this embodiment configured as above, effects similar to those of the first embodiment can be achieved.

Fourth Embodiment

A fourth embodiment in accordance with the present invention will be described below with reference to FIGS. 10 and 11.

Figure 10:
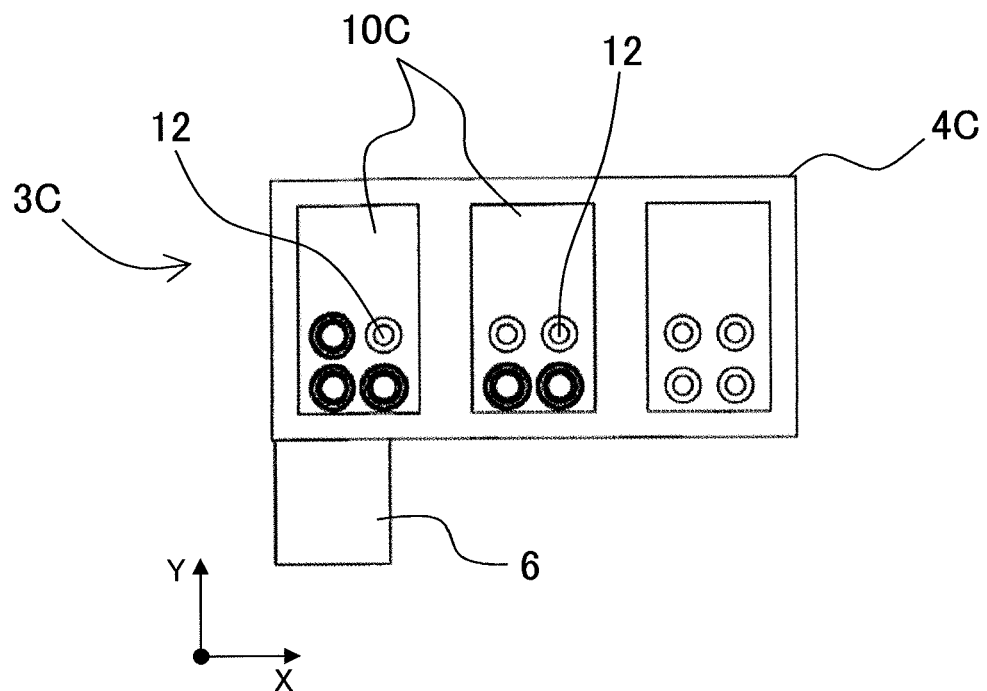
FIG. 10 is a plan view showing a nucleic acid amplifier in accordance a fourth embodiment of the present invention.
Figure 11:
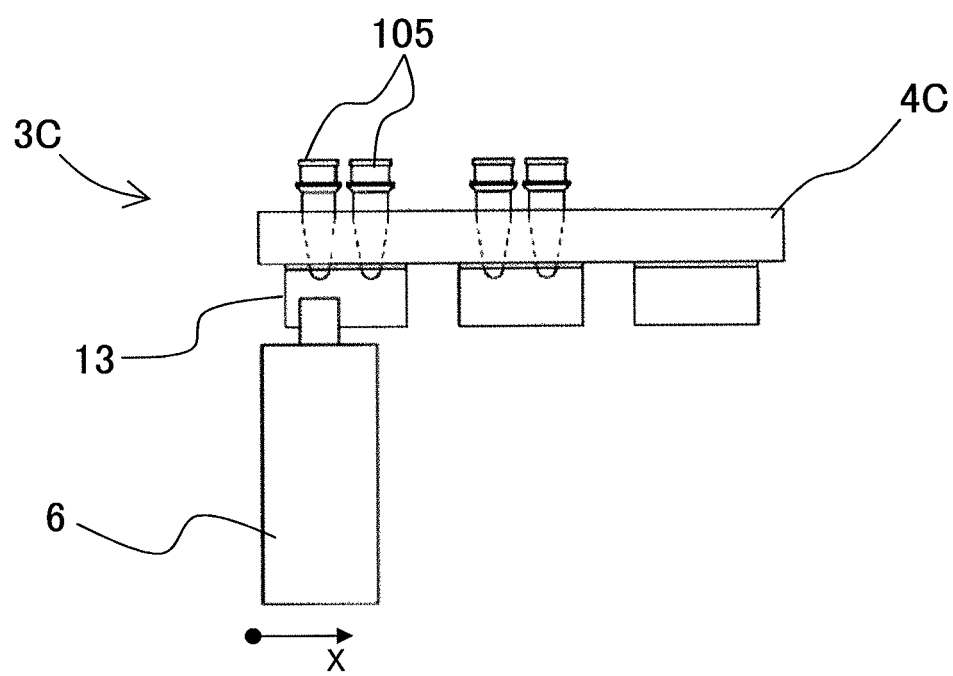
FIG. 11 is a side view showing the nucleic acid amplifier in accordance the fourth embodiment of the present invention.

FIGS. 10 and 11 are a plan view and a side view showing a holder 3C in accordance with this embodiment. In FIGS. 10 and 11, components identical with those explained in the first embodiment are assigned the same reference characters as in the first embodiment and repeated explanation thereof is omitted for brevity. In this embodiment, a holder 3C not in a disk shape is employed instead of the holder 3 in the first embodiment.

Referring to FIGS. 10 and 11, the holder 3C in this embodiment includes a rectangular plate-like holder base 4C arranged with its planar part facing upward and a plurality of temperature control blocks 10C arranged in a line on the holder base 4C. Each temperature control block 10C is provided with a plurality of (four in this embodiment) setting positions 12. Although not shown in the figures, similarly to the configuration shown in FIG. 4 in the first embodiment, each temperature control block 10C is equipped with a Peltier element and a radiation fin for serving as a temperature control device and a temperature sensor for detecting the temperature of the reaction solutions in the reaction vessels 105 by measuring the temperature in the vicinity of the setting positions 12. A fluorescence detector 6 is placed below the reaction vessels 105 (below the path of the movement of the reaction vessels 105) and detects fluorescence when a reaction vessel 105 passes over the fluorescence detector 6 due to the driving of the holder 3C. The holder base 4C is arranged to be movable in the X-axis direction (horizontal direction in FIGS. 10 and 11) and in the Y-axis direction (vertical direction in FIG. 10) and to be driven linearly by not shown driving devices.

The other configuration is equivalent to that in the first embodiment.

Also in this embodiment configured as above, effects similar to those of the first embodiment can be achieved.

Other Embodiments

While several embodiments in accordance with the present invention have been described above, a variety of design changes and combinations are possible within the spirit and scope of the present invention.

For example, while the temperature control blocks are provided on the holder base of the holder in the first and second embodiments, the configuration with the notch parts formed between the temperature control blocks may also be employed similarly to the third embodiment. In the first and second embodiments, the heat radiation/absorption efficiency of the Peltier element of each temperature control block may be increased by forming the holder base with a thermal conductor, providing the temperature control device, and keeping the holder base at a constant temperature (e.g., 40° C.) similarly to the third embodiment.

While a radiation fin is provided for enhancing the heat radiation efficiency of the Peltier element of the temperature control device in the above embodiments of the present invention, the configuration for enhancing the heat radiation efficiency of the Peltier element is not restricted to this example. For example, the heat radiation efficiency of the Peltier element may be enhanced by water cooling, by providing a pipe line for circulating a coolant instead of the radiation fin.

Figure 12:
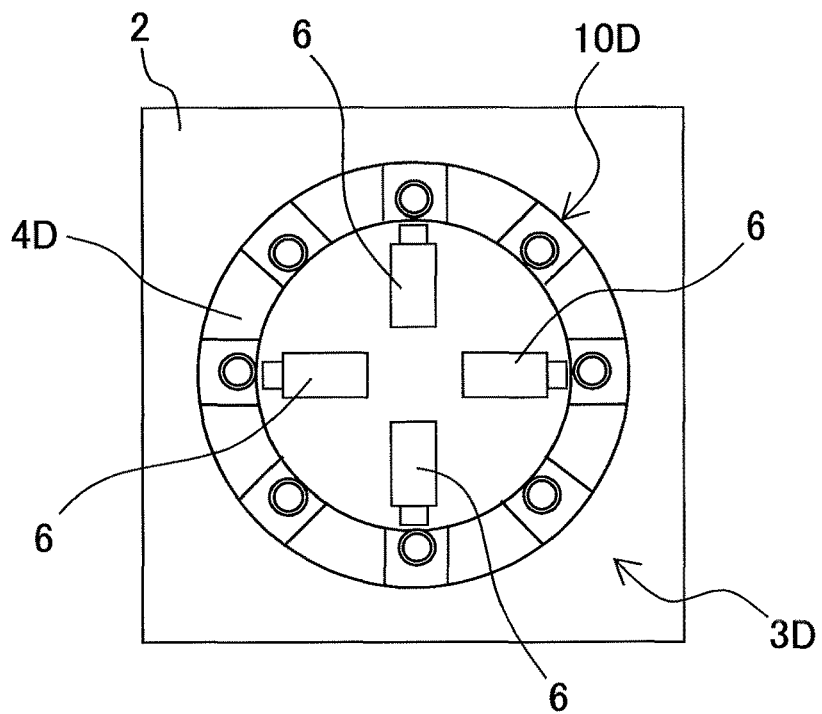
FIG. 12 is a plan view showing a nucleic acid amplifier in accordance a modification of an embodiment of the present invention.
Figure 13:
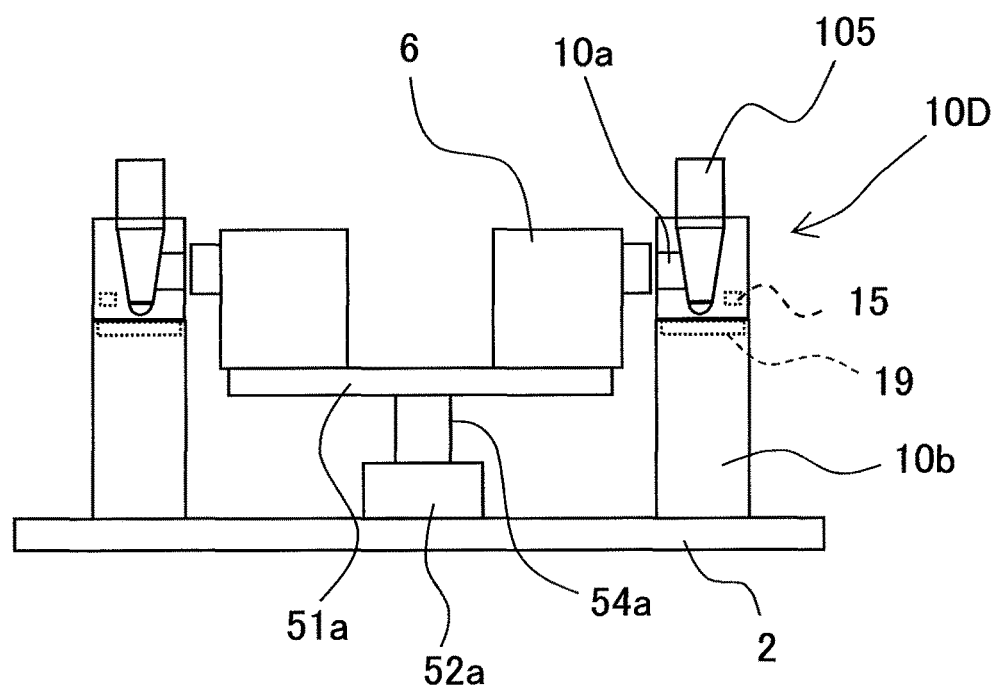
FIG. 13 is a transparent side view showing a nucleic acid amplifier in accordance a modification of an embodiment of the present invention.

While the fluorescence detection is performed in the above embodiments by irradiating each reaction vessel 105 held in a setting position 12 with the excitation light from below, the configuration for irradiating the reaction vessels 105 with the excitation light is not restricted to this example. For example, a configuration shown in FIGS. 12 and 13 may be employed, wherein reaction vessels 105 arranged on a holder base 4D are fixed by fixed holders 10b, while detectors 6 are arranged on a detector base 51a that can be rotated by a motor 52a around a detector base rotating shaft 54a. The irradiation with the excitation light and the detection of the fluorescence are performed from the inside of the holder base 4D via detection windows 10a.

It is also possible to irradiate each reaction vessel 105 with the excitation light from below, from above, or from the side of the reaction vessel 105 and perform the fluorescence detection in a direction differing from the irradiating direction of the excitation light.

It goes without saying that the various methods described in the above embodiments of the present invention can be employed selectively so that the method for setting the reaction vessels 105 and the timing are optimized for each purpose of use of the device.

DESCRIPTION OF REFERENCE CHARACTERS 1 nucleic acid amplifier
2 base
3, 3A, 3B, 3C, 3D holder
4, 4A, 4B, 4C, 4D holder base
5 stepping motor
5a rotating shaft
6 fluorescence detector
7 cover
7a gate
10, 10A, 10B, 10C, 10D temperature control block
10a detection window
10b fixed holder
11 base
12 setting position
13 radiation fin
14, 17, 18, 19 Peltier element
15, 15a temperature sensor
16 notch part
40 fan
41 radiation fin
51, 51a detector base
52, 52a motor
53 belt
54, 54a detector base rotating shaft
55 support member
100 nucleic acid inspection device
101 sample vessel
102 sample vessel rack
103 reagent vessel
104 reagent vessel rack
105 reaction vessel
106 reaction vessel rack
107 reaction solution adjustment position
108 plugging unit
109 stirring unit
110 robot arm X-rail
111 robot arm Y-rail
112 robot arm device
113 gripper unit
114 dispensing unit
115 nozzle chip
116 nozzle chip rack
117 waste box
118 input device
119 display device
120 control device

The invention claimed is:

1. A nucleic acid amplifier for amplifying nucleic acid in a reaction solution as a mixture of a sample and a reagent, comprising:
a holder that is provided with a plurality of temperature control blocks each configured to hold at least one reaction vessel storing a reaction solution;
a temperature control device that is provided in each of the temperature control blocks and is programmed to control a temperature of the reaction solution, such that temperature control is performed at a different temperature and time in each of the temperature control blocks; wherein
the holder has a disk-shaped base arranged with its central axis pointing upward and is rotatable in the circumferential direction;
the temperature control blocks are arranged in a circumferential direction on an outer surface of a periphery of the disk-shaped base, and
the temperature control device includes a plurality of Peltier elements, each having first and second heat exchanging surfaces, arranged so that the first heat exchanging surfaces adhere to the temperature control blocks and the second heat exchanging surfaces adhere to the outer surface of the periphery of the disk-shaped base; and
the disk-shaped base includes a fan and a radiation fin arranged at a center of the disk-shaped base.

2. The nucleic acid amplifier according to claim 1, wherein the nucleic acid amplifier is configured such that reaction vessels each storing a reaction solution as a mixture of a sample and a reagent can be successively loaded into the temperature control blocks.

3. The nucleic acid amplifier according to claim 1, wherein the nucleic acid amplifier is configured such that each reaction vessel for which a prescribed time has passed can be unloaded from the temperature control blocks.

4. The nucleic acid amplifier according to claim 1, wherein at least one of the temperature control blocks is configured such that it can be controlled at a constant temperature during the nucleic acid amplification.

5. The nucleic acid amplifier according to claim 1, wherein the nucleic acid amplifier is configured such that at least one of the temperature control blocks can perform a thermal cycle corresponding to PCR amplification.

6. The nucleic acid amplifier according to claim 1, wherein the reaction vessels are arranged separate from each other.

7. The nucleic acid amplifier according to claim 1, wherein the reaction vessels are thermally insulated from each other.

8. The nucleic acid amplifier according to claim 1, wherein each temperature control block is detachable from the base member.

9. The nucleic acid amplifier according to claim 1, wherein at least one of the temperature control blocks is configured so that a reaction vessel in a different shape can be set therein.

10. The nucleic acid amplifier according to claim 1, wherein at least one of the temperature control blocks differ in material and in the temperature control device.

11. The nucleic acid amplifier according to claim 1, further comprising a cover which blocks external light.

12. The nucleic acid amplifier according to claim 11, wherein the cover is provided with a loading part to be used for loading the reaction vessels into the inside of the cover.

13. The nucleic acid amplifier according to claim 1, wherein: the nucleic acid amplifier is configured such that a position for loading in the reaction vessels can be preset, and the base member rotates to the preset loading position when a reaction vessel should be loaded in.

14. The nucleic acid amplifier according to claim 1, wherein the nucleic acid amplifier is configured such that each reaction vessel can be loaded in an arbitrarily specified reaction vessel setting position.

15. The nucleic acid amplifier according to claim 1, further comprising:

at least one fluorescence detector which detects fluorescence caused by irradiation of the reaction solution in the reaction vessel with excitation light emitted from a light source;

wherein the temperature control blocks are arranged to be movable with respect to the fluorescence detector.

16. The nucleic acid amplifier according to claim 15, comprising a plurality of fluorescence detectors which perform the fluorescence detection independently from each other.

17. The nucleic acid amplifier according to claim 15, wherein the fluorescence detector is arranged to be movable with respect to the temperature control blocks.

18. The nucleic acid amplifier according to claim 15, wherein the temperature control blocks are arranged to be relatively movable with respect to the fluorescence detector that is movable.

19. The nucleic acid amplifier according to claim 1, wherein the base member is formed of members excelling in heat insulating properties compared to the temperature control blocks.

20. The nucleic acid amplifier according to claim 1, wherein the base member is formed of members excelling in heat conductivity.

21. A nucleic acid amplifier for amplifying nucleic acid in a reaction solution as a mixture of a sample and a reagent, comprising:
  a holder that is provided with a plurality of temperature control blocks each configured to hold at least one reaction vessel containing a reaction solution;
  a temperature control device that is provided in each of the plurality of temperature control blocks and is programmed to control a temperature of the reaction solution, such that temperature control is performed at a different temperature and time in each of the temperature control blocks; wherein
  the holder has a ring-shaped base arranged with its central axis pointing upward and is fixed to a base of the nucleic acid amplifier,
  the plurality of temperature control blocks are arranged in a circumferential direction on an outer surface of a periphery of the ring-shaped base on an uppermost surface of the ring-shaped base, and
  the temperature control device includes a plurality of Peltier elements, each having first and second heat exchanging surfaces, arranged so that the first heat exchanging surfaces adhere to the temperature control blocks and the second heat exchanging surfaces adhere to the ring-shaped base; and
  a plurality of fluorescence detectors arranged around a periphery of a rotatable detector base inside of the ring-shaped base of the holder; and
  the ring-shaped base includes a fan and a radiation fin arranged at a center of the ring-shaped base.

22. The nucleic acid amplifier according to claim 20, wherein heat capacity of the base member is larger than that of the temperature control blocks.

23. The nucleic acid amplifier according to claim 1, further comprising a temperature control unit which controls the temperature of the base member.

24. The nucleic acid amplifier according to claim 23, wherein the temperature control unit controls the temperature of the base member at temperatures lower than temperature control ranges of the temperature control devices of the temperature control blocks.

25. The nucleic acid amplifier according to claim 1, wherein the plurality of temperature control blocks are arranged with an open space between adjacent temperature control blocks to allow for airflow therebetween.

* * * * *